United States Patent [19]
Mewshaw et al.

[11] Patent Number: 6,150,533
[45] Date of Patent: Nov. 21, 2000

[54] N-ARYLOXYETHYL-INDOLY-ALKYLAMINES FOR THE TREATMENT OF DEPRESSION

[75] Inventors: Richard E. Mewshaw, Princeton, N.J.; James A. Nelson, Washington Crossing, Pa.

[73] Assignee: American Home Products Corp., Madison, N.J.

[21] Appl. No.: 09/287,832

[22] Filed: Apr. 7, 1999

Related U.S. Application Data

[60] Provisional application No. 60/104,587, Apr. 8, 1998.

[51] Int. Cl.$^7$ ........... C07D 235/04; C07D 235/22; C07D 209/48; A61K 31/4184; A61K 31/404; A61N 25/24

[52] U.S. Cl. ........... 548/305.1; 514/394; 514/415; 514/418; 548/305.7; 548/306.7; 548/457; 548/462

[58] Field of Search ............ 548/305.1, 305.7, 548/306.7, 457, 462; 514/394, 415, 418

[56] References Cited

U.S. PATENT DOCUMENTS

| | | | |
|---|---|---|---|
| 3,371,098 | 2/1968 | Kralt et al. | 514/415 X |
| 4,873,346 | 10/1989 | Anderson | 548/157 |
| 4,954,502 | 9/1990 | Smith et al. | |
| 5,338,756 | 8/1994 | Fortin et al. | 514/394 |
| 5,436,264 | 7/1995 | Pfister et al. | 514/415 |
| 5,541,204 | 7/1996 | Sher et al. | 514/359 |
| 5,693,652 | 12/1997 | Takase et al. | 514/322 |
| 5,885,987 | 3/1999 | Timmerman et al. | 514/224.2 |

FOREIGN PATENT DOCUMENTS

| | | |
|---|---|---|
| 0303506 | 2/1989 | European Pat. Off. |
| 0478954 | 4/1992 | European Pat. Off. |
| 0714894 | 6/1996 | European Pat. Off. |
| 0722941 | 7/1996 | European Pat. Off. |
| 0812826 | 12/1997 | European Pat. Off. |
| 19615232 | 10/1997 | Germany |
| 5255302 | 10/1993 | Japan |
| 9040648 | 2/1997 | Japan |
| WO 9808819 | 3/1988 | WIPO |
| WO 9112252 | 8/1991 | WIPO |
| WO 9808817 | 3/1998 | WIPO |
| WO 9828293 | 7/1998 | WIPO |

OTHER PUBLICATIONS

Artigas et al., *Trends Neurosci.*, 19:378–383 (1996).

Dirk, R. et al: "Synthesis of (11C0 RPR–72840A and Its Evaluation as a Radioligand for the Serotonin Reuptake Site In Positron Emission Tomography", *Chemical Abstract & Indexes*, 126(20) (1997). Abstract.

Nelson, D. L., *Pharmacology Biochemistry & Behavior*, 40(4):1041–51 (1991).

Sleight, A.J. et al., "Identification of 5–hydroxytryptamine 1A Receptor Agents Using A Composite Pharmacophore Analysis and Chemical Database Screening", *Naunyn–Schmiedeberg's archives of Pharmacology*, 343:109–16 (1991).

Glennon, R. A., "Concepts for the design of %–HT1A Serotonin agonists and antagonists", *Drug Development Research*, 26(3):251–274 (1992).

Cliffe, I. A. et al., *Drugs of the Future*, 18(7):631–42 (1993).

*Primary Examiner*—Floyd D. Higel
*Attorney, Agent, or Firm*—Michael R. Nagy

[57] ABSTRACT

Compounds effective in treating disorders of the serotonin-affected neurological systems are provided, such compounds having the following formula:

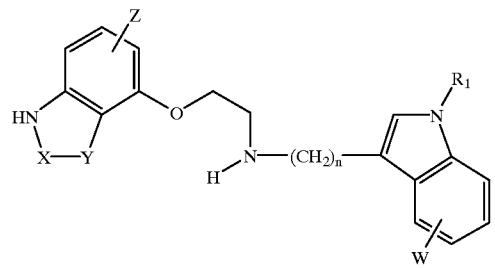

wherein:

$R_1$ is hydrogen, lower alkyl, phenyl, or substituted phenyl;

X and Y together complete a lactam, imidazole, imidazolone, or thioimidazolone ring;

Z is hydrogen, halogen, or lower alkoxy;

W is hydrogen, halogen, lower alkoxy, lower alkyl, cyano, or a trifluoromethyl group;

and n=2 to 5; or pharmaceutically acceptable salts thereof.

10 Claims, No Drawings

N-ARYLOXYETHYL-INDOLY-ALKYLAMINES FOR THE TREATMENT OF DEPRESSION

CROSS REFERENCE TO RELATED APPLICATIONS

This application claims the benefit of U.S. Provisional Application No. 60/104,587, which was converted from U.S. patent application No. 09/057,159, filed Apr. 8, 1998, pursuant to a petition filed under 37 C.F.R. 1.53(c)(2)(i) filed May 12, 1998.

FIELD OF INVENTION

This invention relates to compounds useful for the treatment of diseases affected by disorders of the serotonin-affected neurological systems, such as depression and anxiety. More specifically, this invention relates to various N-aryloxyethyl-indoly-alkylamnines useful for the treatment of such diseases.

BACKGROUND OF INVENTION

Pharmaceutical compounds which enhance the transmission of serotonin (5-HT) are useful for the treatment of many psychiatric disorders, including depression and anxiety. The first generation of non-selective serotonin-affecting drugs operated through a variety of physiological functions which cause them to possess numerous undesired side effects, such as blurred vision, dry mouth, and sedation. The more recently introduced compounds, the selective serotonin reuptake inhibitors (SSRIs), act predominately by inhibiting 5-HT, which is released at the synapses, from being actively removed from the synaptic cleft via a presynaptic serotonin transport carrier. As SSRIs require several weeks before they exert their full therapeutic effect, this 5-HT blockade mechanism cannot fully account for their therapeutic activity. It is speculated that this two week induction which occurs before a full antidepressant effect is observed, is due to the involvement of the 5-HT1A autoreceptors which suppress the firing activity of the 5-HT neurons, causing a dampening of the therapeutic effect. Studies suggest that after several weeks of SSRI administration, a desensitization of the 5-HT autoreceptors occurs allowing a full antidepressant effect in most patients. Hence, it is believed that overriding this negative feedback by using 5-HT1A antagonists would potentially increase and accelerate the clinical antidepressant response. Recent studies by Artigas et al., *Trends Neurosci.*, 19:378–383 (1996) suggest a combination of 5-HT1A activity and inhibition of 5-HT uptake within a single molecular entity can achieve a more robust and fast-acting antidepressant effect.

For example, U.S. Pat. No. 3,371,098 discloses sec. and tert. indolylethylamines useful as sedatives, anticonvulsants and analgesics.

U.S. Pat. No. 5,436,264 discloses N-aryloxyalkyl-tryptamine-like compounds of the following formula as alpha-1-adrenergic receptor antagonists for the treatment of cardiovascular disorders.

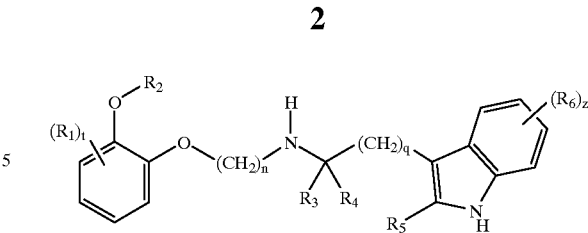

European Patent No. 0722 941 A2 discloses the preparation of a series of hetero-oxy alkanamines of the following formula for the treatment of depression and other conditions for which serotonin uptake inhibitors are used.

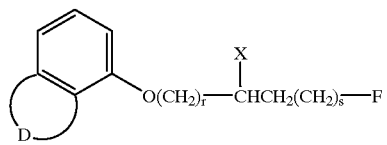

Japanese Patent Nos. 05255302 and 09040648 disclose the following compounds which are useful for the treatment of central nervous system-related diseases, such as anxiety and depression.

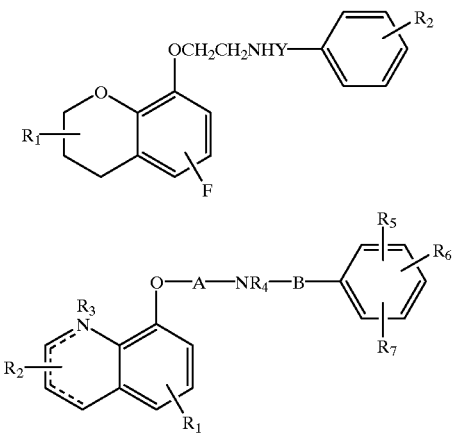

SUMMARY OF THE INVENTION

The present invention relates to a new class of molecules which have the ability to act concomitantly at the 5-HT1A autoreceptors and with the 5-HT transporter. Such compounds are therefore potentially useful for the treatment of depression as well as other serotonin disorders.

The compounds of the present invention are N-aryloxyethyl-indoly-alkylamines represented by Formula I:

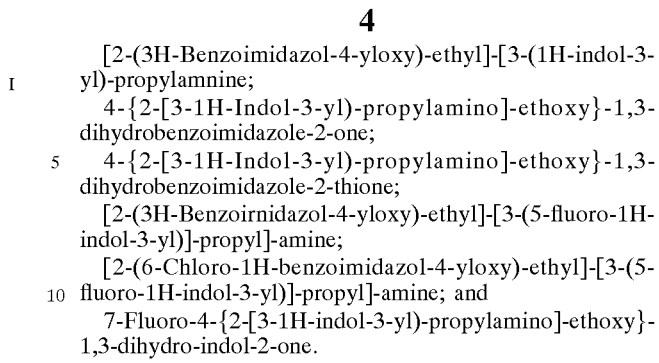

wherein:

R₁ is hydrogen, lower alkyl, phenyl, or substituted phenyl;

X and Y together complete a lactam, imidazole, imidazolone, or thioimidazolone ring;

Z is hydrogen, halogen, or lower alkoxy;

W is hydrogen, halogen, lower alkoxy, lower alkyl, cyano, or a trifluoromethyl group; and n=2 to 5; or pharmaceutically acceptable salts thereof.

DETAILED DESCRIPTION OF THE INVENTION

Preferably, the compounds of the present invention are those represented by Formula I, wherein:

R₁ is hydrogen;

X and Y together complete an imidazole or thioimidazolone ring;

Z is halogen or hydrogen;

W is halogen or hydrogen; and n=2 to 3; or pharmaceutically acceptable salts thereof.

More preferably, the compounds of the present invention are selected form the following:

[2-(3H-Benzoimidazol-4-yloxy)-ethyl]-[3-(1H-indol-3-yl)-propylamnine;

4-{2-[3-1H-Indol-3-yl)-propylamino]-ethoxy}-1,3-dihydrobenzoimidazole-2-one;

4-{2-[3-1H-Indol-3-yl)-propylamino]-ethoxy}-1,3-dihydrobenzoimidazole-2-thione;

[2-(3H-Benzoirnidazol-4-yloxy)-ethyl]-[3-(5-fluoro-1H-indol-3-yl)]-propyl]-amine;

[2-(6-Chloro-1H-benzoimidazol-4-yloxy)-ethyl]-[3-(5-fluoro-1H-indol-3-yl)]-propyl]-amine; and 7-Fluoro-4-{2-[3-1H-indol-3-yl)-propylamino]-ethoxy}-1,3-dihydro-indol-2-one.

As used herein, the terms "lower alkyl" and "lower alkoxy" are meant to include straight and branched carbon chains containing 1 to 6 carbon atoms. The term "halogen" is meant to include fluorine, chlorine, bromine and iodine.

The compounds of Formula I also may advantageously be used in the form of a pharmaceutically acceptable acid addition salt having the utility of the free base. Such salts, which may be prepared by methods well known to those skilled in the art are formed with both inorganic or organic acids, for example: fumaric, maleic, benzoic, ascorbic, pamoic, succinic, bismethylenesalicylic, methanesulfonic, ethanedisulfonic, acetic, oxalic, propionic, tartaric, salicyclic, citric, gluconic, lactic, malic, mandelic, cinnamic, citraconic, aspartic, stearic, palmitic, itaconic, glycolic, p-aminobenzoic, glutamic, benzene-sulfonic, hydrochloric, hydrobromic, sulfuric, cyclohexylsulfamic, phosphoric and nitric acids.

The compounds of the present invention may be prepared by any suitable method known to those skilled in the art. However, the compounds may be advantageously prepared according to any one of Schemes 1 to 4 below. In the Schemes, the intermediate compounds exemplified hereinafter are identified in parentheses. The compound produced in each of Schemes 1 to 4 is identified by reference to the appropriate Example.

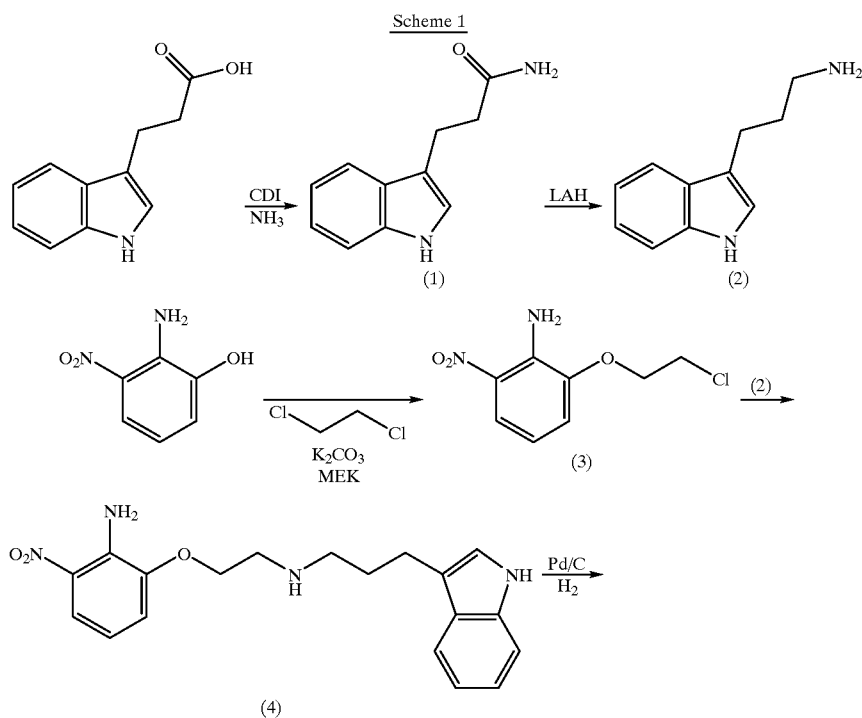

Scheme 1

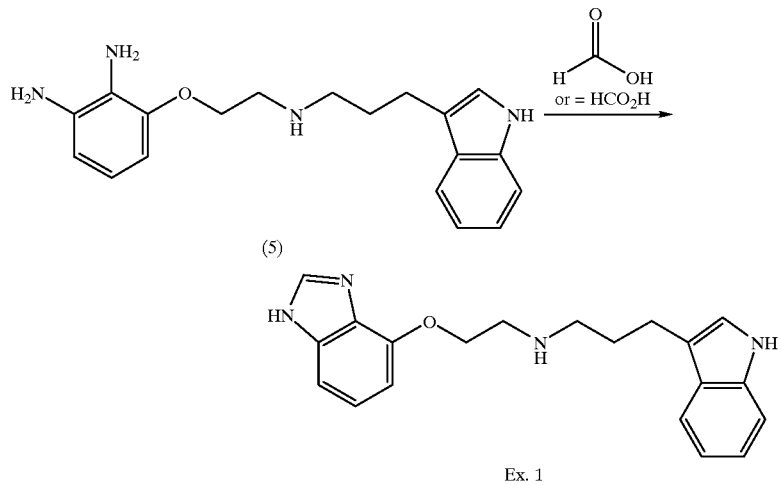
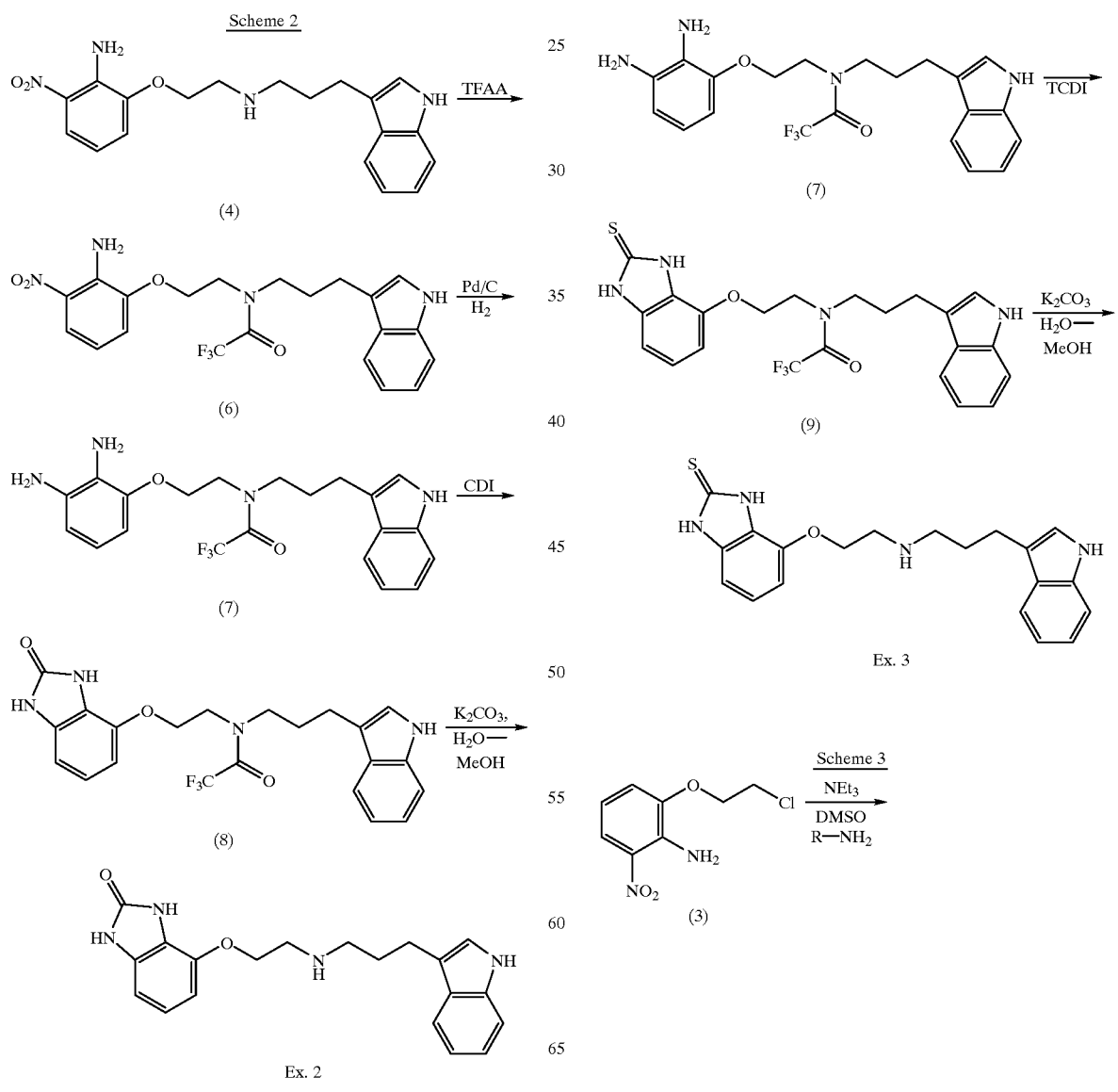

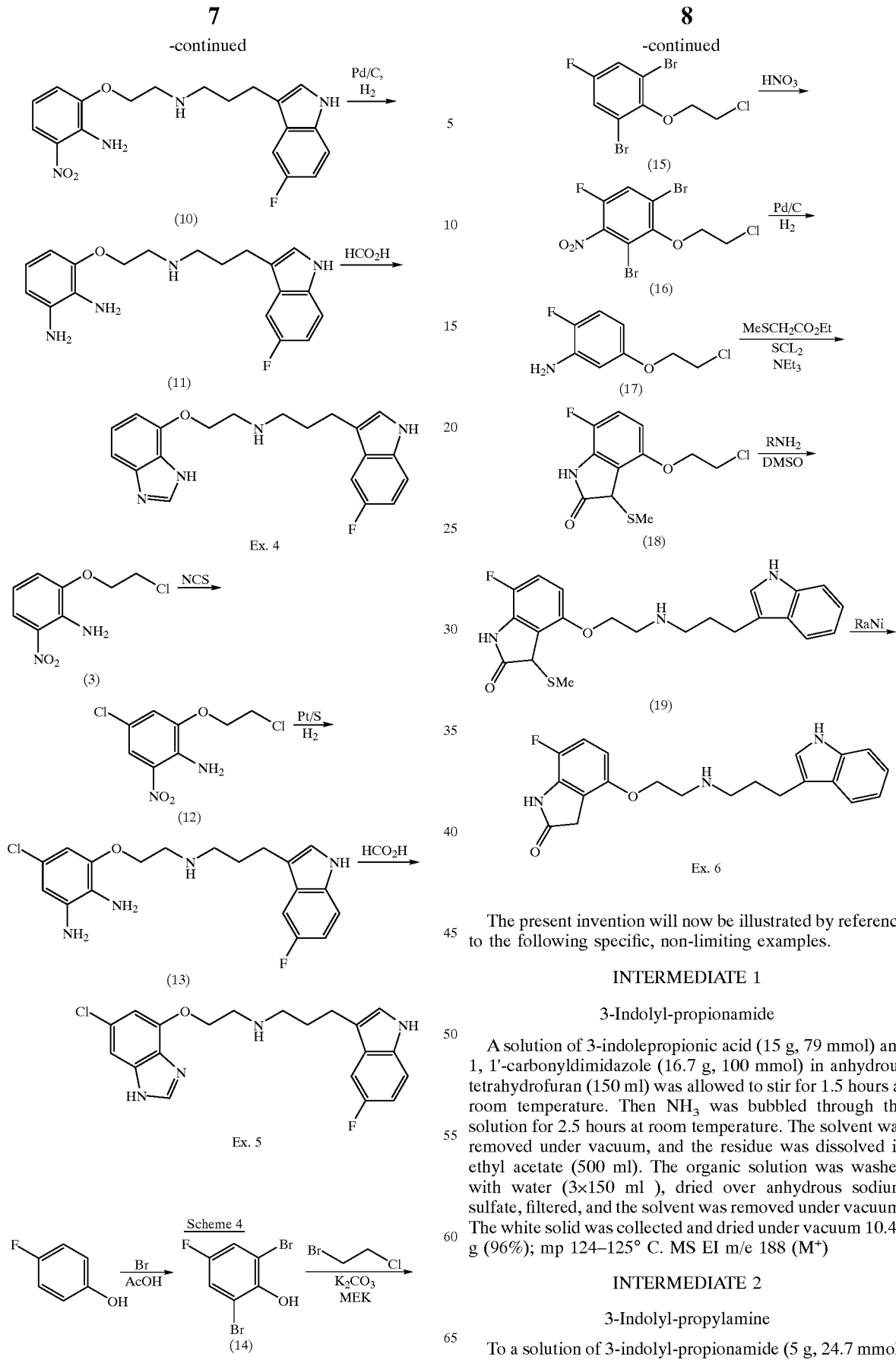

The present invention will now be illustrated by reference to the following specific, non-limiting examples.

INTERMEDIATE 1

3-Indolyl-propionamide

A solution of 3-indolepropionic acid (15 g, 79 mmol) and 1, 1'-carbonyldimidazole (16.7 g, 100 mmol) in anhydrous tetrahydrofuran (150 ml) was allowed to stir for 1.5 hours at room temperature. Then $NH_3$ was bubbled through the solution for 2.5 hours at room temperature. The solvent was removed under vacuum, and the residue was dissolved in ethyl acetate (500 ml). The organic solution was washed with water (3×150 ml ), dried over anhydrous sodium sulfate, filtered, and the solvent was removed under vacuum. The white solid was collected and dried under vacuum 10.42 g (96%); mp 124–125° C. MS EI m/e 188 ($M^+$)

INTERMEDIATE 2

3-Indolyl-propylamine

To a solution of 3-indolyl-propionamide (5 g, 24.7 mmol) in anhydrous tetrahydrofuran (150 ml) was added lithium aluminum hydride (1.0 M solution in tetrahydrofuran, 100 ml) slowly. The reaction mixture was refluxed for 3 hours, and then quenched sequentially with water (4 ml), 15% sodium hydroxide (4 ml), and water (12 ml) at 0° C. The mixture was filtered through celite and concentrated under vacuum. Chromatography (10% methanol-methylene chloride plus ammonium hydroxde) afforded 4.0 g (86%) of product as a white solid: mp 58–60.5° C.; MS EI m/e 174 (M$^{.+}$).

INTERMEDIATE 3

2-(2-Chloro-ethoxy)-6-nitro-phenylamine

A slurry containing 2-amino-3-nitrophenol (32.0 g, 0.208 mol), 1,2-dichloroethane (260.0 g, 2.65 mol), potassium carbonate (35.0 g, 0.252 mol) and 2-butanone (750 ml) was refluxed for 24 hours. The mixture was cooled and filtered and the solids were washed with ethyl acetate. The filtrate was concentrated to an oily residue that was dissolved in ethyl acetate (500 ml). The organic layer was washed with 1 N sodium hydroxide (250 ml), water (500 ml) and brine (2×500 ml) and then dried over anhydrous magnesium sulfate. Concentration of the filtered solution and trituration of the residue with hexanes afforded 37.8 g (84.6%) of product as an orange solid: mp 71–73° C.; MS EI m/e 216 (M$^+$).
Elemental analysis for $C_8H_9ClN_2O_3$
  Calc'd: C, 44.36; H, 4.19; N, 12.93
  Found: C, 44.45; H, 4.02; N, 12.97

INTERMEDIATE 4

2-{2-[3-(1H-Indol-3-yl)-propylamino]-ethoxy}-6-nitro-phenylamine

A solution containing 2-(2-chloro-ethoxy)-6-nitro-phenylamine (4.1 g, 19 mmol) and 3-(1H-indol-3-yl)-propylamine (7.1 g, 40.8 mmol) in anhydrous dimethylsulfoxide (50 ml) was heated at 60° C. for 12 hours. Ethyl acetate (200 ml) was added and the mixture was washed with saturated sodium bicarbonate (3×200 ml) and brine (200 ml). The organic layer was dried over anhydrous magnesium sulfate, filtered and concentrated to give a crude product. Purification by chromatography (ethyl acetate:hexanes:2N ammonia methanol=25:25:1) afforded 4.6 g (68.9%) of the product as a yellowish red viscous oil; MS EI m/e 354 (M$^+$).
Elemental analysis for $C_{19}H_{22}N_4O_3 \cdot 0.4H_2O \cdot 0.1C_4H_8O_2 \cdot 0.05CH_2Cl_2$
  Calc'd: C, 62.35; H, 6.38; N, 14.95
  Found: C, 62.38; H, 6.30; N, 14.90

INTERMEDIATE 5

3-{2-[3-(1H-Indol-3-yl)-propylamino]-ethoxy}-benzene-1,2-diamine

To a solution of the 2-{2-[3-(1H-indol-3-yl)-propylamino]-ethoxy}-6-nitro-phenylamine (1.9 g, 5.39 mmol) in ethanol (40 ml) was added 5% palladium on carbon (0.5 g) under nitrogen. The resulting slurry was hydrogenated under 40 psi for 4 hours. The catalyst was removed by filtration and the ethanol evaporated to afford the crude product. Purification by chromatography (3–10% 2N ammonia methanol in methylene chloride) gave 1.57 g (90.6%) of product as a brown oil. $^1$H NMR (400 MHZ, DMSO-d6), δ1.79, (2H, q, J=7.2 Hz); 2.62, (2H, t, J=7.1 Hz); 2.71, (2H, t, J=7.2 Hz); 2.83, (2H, t, J=5.2 Hz); 4.09, (2H, br); 4.43, (2H, br); 6.19, (1H, t, J=8.0 Hz); 6.33, (1H, t, J=7.9 Hz); 6.94; (1H, t, J=7.0 Hz); 7.03, (1H, t, J=7.2 Hz); 7.08, (1H, d, J=2.0 Hz); 7.29, (2H, d, J=7.4 Hz); 7.31, (2H, d, J=7.4 Hz); 10.7, (1H, br).

INTERMEDIATE 6

N-[2-(2-Amino-3-nitro-phenoxy)-ethyl]-2,2,2-trifluoro-N-[3-(1H-indol-3-yl)-propyl]-acetamide To a solution containing triethylamine (3.15 ml, 22.6 mmol) and 2-{2-[3-(1H-indol-3-yl)-propylamino]-ethoxy}-6-nitro-phenylamine (4.0 g, 11.3 mmol) in methylene chloride (60 ml) at 60° C. was added slowly trifluoroacetic anhydride (1.88 ml, 13.3 mmol). The mixture was stirred at room temperature for two 2 hours. The solvent was removed under vacuum and the residue was partitioned between ethyl acetate (100 ml) and saturated sodium bicarbonate (100 ml). The organic layer was separated and washed with water (100 ml) and brine (100 ml) and then dried over anhydrous magnesium sulfate. Concentration to give crude product, followed by purification by chromatography, gave 3.5 g (69.1%) of product as a viscous reddish orange oil; MS EI m/e 450 (M$^+$).

INTERMEDIATE 7

N-[2-(2,3-Diamino-phenoxy)-ethyl]-2,2,2-trifluoro-N-[3-(1H-indol-3-yl)-propyl]-acetamide To a solution containing N-[2-(2-amino-3-nitro-phenoxy)-ethyl]-2,2,2-trifluoro-N-[3-(1H-indol-3-yl)-propyl]-acetamide (3.86 g, 8.57 mmol) in ethanol (40 ml) under nitrogen was added 10% palladium on carbon (1 g). The mixture was hydrogenated at 40 psi for 6 hours. The catalyst was filtered, washed with ethanol and the filtrate was concentrated to give the crude product. Purification by chromatography (40% ethyl acetate-hexanes) afforded 2.8 g (78.8%) of product as a viscous brown oil; MS EI m/e 420 (M$^+$).

INTERMEDIATE 8

2,2,2-Trifluoro-N-[3-(1H-indol-3-yl)-propyl]-N-[2-(2-oxo-2,3-dihydro-1H-benzoimidazol-4-yloxy)-ethyl]-acetamide A mixture of N-[2-(2,3-diamino-phenoxy)-ethyl]-2,2,2-trifluoro-N-[3-(1H-indol-3-yl)-propyl]-acetamide (0.5 g, 1.19 mmol) and diimidazole carbonyl (0.39 g, 2.38 mmol) in anhydrous tetrahyrofuran (50 ml) was stirred at 23° C. for 5 hours. The reaction mixture was poured into water and extracted with ethyl acetate (2×250 ml). The organic layer was washed with water (2×250 ml) and brine (200 ml) and dried over anhydrous magnesium sulfate. The resulting product was concentrated to give the crude product. Purification by chromatography (60% ethyl acetate-hexanes) followed by crystallization from ethyl acetate-hexanes afforded 0.44 g (82.9%) of product as yellowish colored solid: mp 180–181° C.; MS EI m/e 446 (M$^+$).
Elemental analysis for $C_{22}H_{21}F_3N_4O_3$
  Calc'd: C, 59.19; H, 4.74; N, 12.55
  Found: C, 58.95; H, 4.82; N, 12.71

INTERMEDIATE 9

2,2,2-Trifluoro-N-[3-(1H-indol-3-yl)-propyl]-N-[2-(2-thioxo-2,3-dihydro-1H-benzoimidazol-4-yloxy)ethyl]-acetamide This compound was prepared in the manner described above for Intermediate 8 utilizing diimidazole thiocarbonyl to afford a product as a yellow solid: mp 120–121° C.; MS (+) FAB m/e 463 (M+1)$^+$.
Elemental analysis for $C_{22}H_{21}F_3N_4O_2S.0.33C_4H_{10}O$
  Calc'd: C, 57.40; H, 4.99; N, 11.50
  Found: C, 57.42; H, 4.93; N, 11.33

INTERMEDIATE 10

2-{2-[3-(5-Fluoro-1H-indol-3-yl)-propylamino]-ethoxy}-6-nitro-phenylamine

A solution of 2-(2-chloro-ethoxy)-6-nitro-phenylamine (0.5 g, 2.3 mmol), 3-(5-fluoro-1H-3-yl)-propylamine (1.1 g, 5.7 mmol) and triethylamine (0.58 g, 5.7 mmol) in anhydrous dimethylsulfoxide (20 ml) was allowed to stir for 12 hours at 90° C. The mixture was poured into water (100 ml) and extracted with methylene chloride (3×100 ml). The organic layer was washed with water (3×150 ml), dried over anhydrous sodium sulfate and filtered and the solvent was removed under vacuum. Chromatography (5% methanol-methylene chloride plus ammonium hydroxide) afforded 0.67 g (78%) of product as a yellow oil; MS (EI) 358 m/e (M$^+$).

INTERMEDIATE 11

3-{2-[3-(5-Fluoro-1H-indol-3-yl)-propylamino]-ethoxy}-benzene-1,2-diamine

A mixture of 2-{2-[3-(5-fluoro-1H-indol-3-yl)-propylamino]-ethoxy}-6-nitro-phenylamine (0.65 g, 1.7 mmol) and 10% palladium on carbon in ethanol was hydrogenated for 3 hours. The catalyst was filtered off and the solvent removed under vacuum. Chromatography (10% methanol-methylene) afforded 0.49 g (82%) of product as a light-brown oil; MS (EI) 358 m/e (M$^+$).

INTERMEDIATE 12

2-(2-Chloro-ethoxy)-4-chloro-6-nitro-phenylamine

A solution of 2-(2-chloro-ethoxy)-6-nitro-phenylamine (30.0 g, 0.14 mol), N-chlorosuccinimide and acetonitrile (1.3 L) was refluxed for 4 hours. The mixture was concentrated under vacuum and the residue was diluted with ethyl acetate (500 ml). The organic layer was washed with water (2×250 ml) and brine (250 ml), dried over anhydrous magnesium sulfate and filtered. The solvent was removed under vacuum to give an orange solid residue. Crystallization from ethyl acetate-hexanes gave 33.5 g (95.3%) of product as an orange solid: mp 109–110° C.; MS (EI) 250/252/254 m/e (M$^+$).
Elemental analysis for $C_8H_8Cl_2N_2O_3$
  Calc'd: C, 38.27; H, 3.21; N, 11.16
  Found: C, 38.15; H, 3.10; N, 10.96

INTERMEDIATE 13

3-{2-[3-(5-Fluoro-1H-indol-3-yl)-propylamino]-ethoxy}-benzene-5-chloro-1,2-diamine A mixture of 2-(2-chloro-ethoxy)-4-chloro-6-nitro-phenylamine (0.65 g, 1.7 mmol) and 5% platinum on sulfide carbon in ethanol was hydrogenated for 1 hour. The catalyst was filtered off and the solvent removed under vacuum. Chromatography (15% methanol-methylene chloride plus ammonium hydroxide) afforded 0.59 g (80%) of product as a yellow oil; MS (EI) 376 m/e (M$^+$).

INTERMEDIATE 14

2,6-Dibromo-4-fluorophenol

To a solution of 4-fluorophenol (25 g, 0.22. mol) in acetic acid (200 mL) at room temperature was slowly added dropwise bromine (78 g, 0.49 mol) while being mechanically stirred. After 1 hour the reaction mixture was poured into ice water (1.5 L) followed by 100 ml of saturated aqueous sodium bisulfate. The solid precipitate was filtered and dried to afford 51.8 g (86.0%) a white solid: mp 54–55° C.; $^1$H NMR (CDCl$_3$) δ5.69 (1H, s, OH), 7.25 (2H, d, J=7.5 Hz); MS EI m/e 268/270/272 (M$^+$).
Elemental analysis for $C_6H_3Br_2FO$
  Calc'd: C, 26.70; H, 1.12;
  Found: C, 26.64; H, 1.07;

INTERMEDIATE 15

1-(2-Chloroethoxy)-2,6-dibromo-4-fluorobenzene

A mixture of 2,6-dibromo-4-fluoro-phenol (55 g, 0.20 mol), potassium carbonate (60 g, 0.43 mol), 1-bromo-2-chloroethane (32.5 g, 0.23 mol) and 2-butanone (500 ml) was heated to reflux for 2 hours and allowed to cool to ambient temperature. The solids were filtered and the solvent was removed under vacuum to afford an oil. The oil was dissolved in diethyl ether (300 ml) and washed with water, dried over anhydrous magnesium sulfate, charcoalized, and filtered through silica gel to afford 65.9 g (97.2%) of product as an oil; MS EI m/e 330/332/334/336 (M$^+$); $^1$H NMR (CDCl$_3$) δ3.89 (2H, t, J=6.1 Hz), 4.23 (2H, t, J=6.1 Hz), 7.28 (2H, d, J=7.5 Hz).

INTERMEDIATE 16

1-(2-Chloroethoxy)-2,6-dibromo-4-fluoro-3-nitrobenzene

To a solution of 1-(2-chloroethoxy)-2,6-dibromo-4-fluorobenzene (65.8 g, 0.20 mol) in concentrated sulfuric acid (165 ml) maintained at room temperature using a water bath was slowly added a solution of nitric acid in sulfuric acid (10 ml HNO$_3$ in 165 ml H$_2$SO$_4$). The reaction was allowed to stir at room temperature for 1 hour then poured into ice (1.5 L) and extracted with methylene chloride (2×300 ml). The combined organic layers were washed with aqueous sodium bicarbonate (150 ml) and dried over anhydrous magnesium sulfate, filtered, and the solvent removed under vacuum to afford 73.3 g (97.1%) a white crystalline solid: mp 56–57° C.; MS EI m/e 375/377/379/381; $^1$H NMR (CDCl$_3$) δ3.91 (2H, t, J=5.9 Hz), 4.29 (2H, d, J=5.9 Hz), 7.54 (8.1 Hz).
Elemental analysis for $C_8H_5Br_2ClFNO_3$
  Calc'd: C, 25.46; H, 1.34; N, 3.71
  Found: C, 25.46; H, 1.20; N, 3.51

INTERMEDIATE 17

1-(2-Chloroethoxy)-4-fluoro-3-aminobenzene

A solution of 1-(2-chloroethoxy)-2,6-dibromo-4-fluoro-3-nitrobenzene (73.2 g, 0.19 mol) in ethanol (1.1 L) containing 7.3 g of 10% palladium on carbon was hydrogenated at 40 psi for 5 days. The catalyst was filtered and the solvent was removed. The residue was dissolved in diethyl ether (300 ml) and washed with saturated aqueous sodium carbonate (200 ml). The organic layer was separated and washed with water, dried over anhydrous magnesium sulfate and filtered. The solvent was removed to afford an oil which solidified to afford 32.5 g (90.0%) of product as a dark solid: mp 42–43° C.; MS EI m/e 189/191 (M$^+$); $^1$H NMR (CDCl$_3$) δ3.40–3.60 (2H, bs, NH$_2$), 3.77 (2H, d, J=6 Hz), 4.14 (2H, d, J=6 Hz), 6.19–6.23 (1 H, m), 6.36 (1H, dd, J=7, 3 Hz), 6.88 (1H, dd, J=11, 9 Hz).

Elemental analysis for $C_8H_9ClFNO$
  Calc'd: C, 50.68; H, 4.78; N, 7.39
  Found: C, 50.46; H, 4.66; N, 7.46

INTERMEDIATE 18

4-(2-Chloroethoxy)-7-fluoro-3-thiomethyl-1,3-dihydro-indol-2-one

To a solution of ethyl (methylthio) acetate (7.2 g, 53.4 mmol) in anhydrous methylene chloride (200 ml) at −78° C. was added sulfuryl chloride (8.1 g„ 59.7 mmol). The mixture was stirred for 20 minutes. A solution of 1-(2-chloroethoxy)-4-fluoro-3-aminobenzene (10.0 g, 52.8 mmol) and Proton Sponge (13.9 g) in methylene chloride (100 ml) was stirred for 2 hours, followed by the addition of triethylamine (6.5 g, 64.5 mmol). The temperature was maintained at −78° C. and the reaction mixture was allowed to stir for 1 hour. After warming to room temperature, the mixture was poured into brine (200 ml) and dried over anhydrous magnesium sulfate, filtered, and the solvent removed to afford an oil. Acetic acid (75 ml) was added to the oil and the mixture was allowed to stand for 18 hours. The solvent was then removed under vacuum. The residue was partitioned between diethyl ether (400 ml) and 2.5 N aqueous hydrochloric acid (150 ml). The organic layer was separated and dried over anhydrous magnesium sulfate, filtered, and the solvent removed to afford a solid. Trituration of the solid with a small amount of diethyl ether (30 ml) afforded 8.8 g (60.5%) of product as a yellow solid: mp 140–141° C.; MS EI m/e 275/277 ($M^+$); $^1$H NMR ($CDCl_3$: δ2.14 (3H, s), 3.79–3.87 (2H, m), 4.25–4.33 (2H, m), 4.35 (1H, s), 6.51 (1H, dd, J=9.1, 3.3 Hz), 6.99 (1H, app. t, J=9.1 Hz), 8.09 (1H, s).
Elemental analysis for $C_{11}H_{11}ClFNO_2S$
  Calc'd: C, 47.92; H, 4.02; N, 5.08
  Found: C, 47.67; H, 3.85; N, 4.85

INTERMEDIATE 19

7-Fluoro-3-thiomethyl-4-{2-[3-(1H-indol-3-yl)-propyl-amino]-ethyl}-1,3-dihydro-indol-2-one A solution of 4-(2-chloroethoxy)-7-fluoro-3-thiomethyl-1,3-dihydro-indol-2-one (1.48 g, 5.4 mmol) and 3-(1H-indol-3-yl)-propylamine (3.19 g, 18.3 mmol) in anhydrous dimethylsulfoxide (20 ml) was allowed to stir for 5 hours at 95–105° C. and another 3 hours at 115° C. The mixture was poured into water (100 ml) and extracted with methylene chloride (3×100 ml). The organic layer was washed with saturated sodium carbonate (3×40 ml) and water (3×100 ml). The organic layer was dried over anhydrous sodium sulfate, filtered, and the solvent was removed under vacuum. Chromatography (5% methanol-methylene chloride) afforded 1.34 g (52%) of product as a brown oil.

EXAMPLE 1

[2-(3H-Benzoimidazol-4-yloxy)-ethyl]-[3-(1H-indol-3-yl)-propyl]-amine

A solution of 3-{2-[3-(1H-indol-3-yl)-propylamino]-ethoxy}-benzene-1,2-diamine (0.75 g, 2.3 mmol) dissolved in 15 ml formic acid (98%) was heated to 104° C. for 6 hours. Upon standing overnight at 25° C., the excess formic acid was removed by vacuum distillaton. Water (100 ml) and ethyl acetate (100 ml) was added thereto. The ethyl acetate layer was separated and washed once with water (50 ml), once with brine (75 ml) and dried over anhydrous magnesium sulfate. Concentration of the solvent gave 0.7 g of product as a brown solid. Purification by chromatography (2 N ammonia in methanol:methylene chloride=20:1.5) and crystallization from ethyl acetate-ethanol afforded 0.345 g (44.8%) of product as a white solid: mp 121–124° C. decomposed. The HCl salt was prepared in ethanol: mp 256–258° C. decomposed.
Elemental analysis for $C_2OH_{22}N_4O.2HCl.0.25H_2O$
  Calc'd: C, 58.33; H, 6.00; N, 13.60
  Found: C, 58.25; H, 5.92; N, 13.38

EXAMPLE 2

4-{2-[3-1H-Indol-3-yl)-propylamino]-ethoxy}-1,3-dihydrobenzoimidazole-2-one

A suspension of potassium carbonate (1.0 g, 7.4 mmol) and 2,2,2-trifluoro-N-[3-(1H-indol-3-yl)-propyl]-N-[2-(2-oxo-2,3-dihydro-1H-benzoimidazol-4-yloxy)ethyl]-acetimide (0.41 g, 0.92 mmol) in methanol-tetrahydrofuran (10 ml, 1:1) and water (3 ml) was heated to reflux for 3 hours. The solvent was evaporated and the residue was dissolved in ethyl acetate (100 ml) and washed with water (80 ml). The organic layer was dried over anhydrous magnesium sulfate, filtered and concentrated to give crude solid product. Crystallization from ethyl acetate-hexanes afforded 0.25 g (77.7%) or product as a yellow solid: mp 130° C.; MS EI m/e 350 ($M^+$). The HCl salt was prepared in ethyl acetate: mp 222.5–224° C.
Elemental analysis for $C_{20}H_{22}N_4O_2.HCl$
  Calc'd: C, 60.55; H, 6.18; N, 13.85
  Found: C, 60.75; H, 6.08; N, 13.69

EXAMPLE 3

4-{2-[3-1H-Indol-3-yl)-propylamino]-ethoxy}-1,3-dihydrobenzoimidazole-2-thione

This compund was prepared in the manner described in Example 2 utilizing 2,2,2-trifluoro-N-[3-(1H-indol-3-yl)-propyl]-N-[2-(2-thioxo-2,3-dihydro-1H-benzoimidazol-4-yloxy)ethyl]-acetamide afforded a product as a white solid. The HCl salt was prepared in ethyl acetate: mp>260° C.
Elemental analysis for $C_{20}H_{22}N_4OS.HCl.0.25H_2O$
  Calc'd: C, 58.96; H, 5.81; N, 13.75
  Found: C, 58.94; H, 5.74; N, 13.51

EXAMPLE 4

[2-(3H-Benzoimidazol-4-yloxy)-ethyl]-[3-(5-fluoro-1H-indol-3-yl)]-propyl]-amine

A solution 3-{2-[3-(5-fluoro-1H-indol-3-yl)-propylamino]-ethoxy}-benzene-1,2-diamine (0.49 g) in formic acid (30 ml) was allowed to reflux for 4 hours. The mixture was poured into sodium hydroxide (1 N, 150 ml) and extracted with ethyl acetate (3×100 ml). The organic layer was dried over anhydrous sodium sulfate and filtered. Chromatography (10% methanol-methylene chloride) afforded 0.25 g (50%) of product as a off-white solid: mp 93–95° C. The oxalate salt was prepared in ethanol: mp 185–187° C.
Elemental analysis for $C_{20}H_{21}FN_4O.2C_2H_2O_4$
  Calc'd: C, 54.13; H, 4.73; N, 10.52
  Found: C, 53.98; H, 4.74; N, 10.49

EXAMPLE 5

[2-(6-Chloro-1H-benzoimidazol-4-yloxy)-ethyl]-[3-(5-fluoro-1H-indol-3-yl)]-propyl]-amine This compound was prepared in the manner described in Example 4 utilizing 3-{2-[3-(5-fluoro-1H-indol-3-yl)- propylamino]-ethoxy}-benzene-1,2-diamine with 3-{2-[3-(5-fluoro-1H-indol-3-yl)-propylamino]-ethoxy}-benzene-5-chloro-1,2-diamine to give the product in 76% yield (0.22 g) as a white solid: mp 96–99° C. The oxalate salt was prepared in ethanol: mp 185–187° C.

Elemental analysis for $C_{20}H_{21}FN_4O.2C_2H_2O_4.2H_2O$
Calc'd: C, 47.81; H, 4.68; N, 9.29
Found: C, 47.85; H, 4.26; N, 7.92

EXAMPLE 6

7-Fluoro-4-{2-[3-1-H-indol-3-yl)-propylamino]-ethoxy}-1,3-dihydro-indol-2-one

A mixture 7-fluoro-3-thiomethyl-4-{2-[3-(1H-indol-3-yl)-propyl-amino]-ethyl}-1,3-dihydro-indol-2-one (1.34 g, 3.5 mmol) and Raney nickel in ethanol (160 ml) was allowed to stir for 5 hours. The catalyst was filtered off and the solvent removed under vacuum. Chromatography (10% methanol-methylene) afforded 0.24 g (19%) of product as a oil. MS (EI) 358 m/e (M+). The fumarate salt was prepared in ethanol: mp 189–190° C.

Elemental analysis for $C_{21}H_{22}FN_3O_2.C_2H_4O_4$
Calc'd: C, 62.11; H, 5.42; N, 8.69
Found: C, 62.16; H, 5.45; N, 8.59

The activity of the present compounds is demonstrated by the following standard pharmacological test procedure.

The PCR cloning of the human 5-$HT_{1A}$ receptor subtype from a human genomic library has been described previously Chanda et al., *Mol. Pharmacol.* 43:516 (1993). A stable Chinese hamster ovary cell line expressing the human 5-$HT_{1A}$ receptor subtype (h5-$HT_{1A}$.CHO cells) was employed throughout this study. Cells were maintained in DMEM supplemented with 10% fetal calf serum, non-essential amino acids and penicillin/streptomycin.

Cells were grown to 95–100% confluency as a monolayer before membranes were harvested for binding studies. Cells were gently scraped from the culture plates, transferred to centrifuge tubes, and washed twice by centrifugation (2000 rpm for 10 min., 4° C.) in buffer (50 mM Tris; pH 7.5). The resulting pellets were aliquoted and placed at –80° C. On the day of assay, the cells were thawed on ice, and resuspended in buffer. Studies were conducted using [$^3$H]8-OH-DPAT as the radioligand. The binding assay was performed in 96 well microtiter plates in a final total volume of 250 µL of buffer. Competition experiments were performed by using 7 concentrations of unlabelled drug and a final ligand concentration of 1.5 nM. Non-specific binding was determined in the presence of 10 µM 5HT. Saturation analysis was conducted by using [$^3$H]8-OH-DPAT at concentrations ranging from 0.3–30 nM. Following a 30 minute incubation at room temperature, the reaction was terminated by the addition of ice cold buffer and rapid filtration using a M-96 Brandel Cell Harvester (Gaithersburg, Md.) through a GF/B filter pre-soaked for 30 minutes in 0.5% polyethyleneimine.

A protocol similar to that used by Cheetham et al., *Neuropharmacol.* 32:737 (1993) was used to determine the affinity of compounds for the serotonin transporter. Briefly, frontal cortical membranes prepared from male Sprague-Dawley rats were incubated with $^3$H-paroxetine (0.1 nM) for 60 min at 25° C. All tubes also contained either vehicle, test compound (one to eight concentrations), or a saturating concentration of fluoxetine (10 µM) to define specific binding. All reactions are terminated by the addition of ice cold Tris buffer followed by rapid filtration using a Tom Tech filtration device to separate bound from free $^3$H-paroxetine. Bound radioactivity was quantitated using a Wallac 1205 Beta Plate® counter. Nonlinear regression analysis was used to determine $IC_{50}$ values which were converted to Ki values using the method disclosed in Cheng and Prusoff, *Biochem. Pharmacol.*, 22:3099 (1973); Ki=IC50/((Radioligand conc.)/(1+KD)).

The [$^{35}$S]-GTPγS binding assay was similar to that used by Lazareno and Birdsall, *Br. J. Pharmacol.* 109:1120 (1993). Briefly, 5-$HT_{1A}$ cloned receptor membrane fragments (as used for 5-$HT_{1A}$ receptor binding assays) were stored at –70° C. until needed. When needed, membranes were rapidly thawed, centrifuged at 40,000×g for 10 minutes and resuspended at 4° C. for 10 minutes in assay buffer (25 mM HEPES, 3 mM $MgCl_2$, 100 mM NaCl, 1 mM EDTA, 10 uM GDP, 500 mM DTT, pH 8.0). These membranes were then incubated for 30 min at 30° C. with [$^{35}$S]GTPgS (1 nM) in the presence of vehicle, test compound (one to eight concentrations), or excess 8-OH-DPAT to define maximum agonist response. All reactions are terminated by the addition of ice cold Tris buffer followed by rapid filtration using a Tom Tech® filtration device to separate bound from free [$^{35}$S]GTPgS. Agonists produce an increase in the amount of [$^{35}$S]GTPgS bound whereas antagonists produce no increase in binding. Bound radioactivity was counted and analyzed as above.

The following assays were performed by incubating the cells with DMEM containing 25 mM HEPES, 5 mM theophylline and 10 µM pargyline for a period of 20 minutes at 37° C. Functional activity was assessed by treating the cells with forskolin (1 uM final concentration) followed immediately by test compound (6 concentrations) for an additional 10 min at 37° C. In separate experiments, 6 concentrations of antagonist were preincubated for 20 min prior to the addition of 10 nM 8-OH-DPAT and forskolin. The reaction was terminated by removal of the media and addition of 0.5 ml ice cold assay buffer. Plates were stored at –20° C. prior to assessment of cAMP formation by a cAMP SPA assay (Amersham).

The compounds tested correspond to those prepared in Examples 1 to 6 above. The results of the procedure are set forth in Table 1.

TABLE 1

| Example No. | 5-$HT_{1A}$ (Ki, nM) | ST ($K_i$, nM,) | GTPγS ED50 (% EMax) | cAMP ED50 (EMax) |
|---|---|---|---|---|
| 1 | 0.87 | 13.0 | 1.55 (76.9%) | — |
| 2 | 3.17 | 2.09 | 6.71 (98.5%) | — |
| 3 | 7.75 | 21 | — | — |
| 4 | 0.69 | 0.39 | 1.35 (80.3%) | 7.2 (87%) |
| 5 | 10.7 | 0.48 | (0%) | (0%) |
| 6 | 39.14 | 12.0 | 169 (49.9%) | — |

As demonstrated by the results set forth above, the compounds of the present invention are active towards 5-HT1A receptors and generally elevate serotonin levels by inhibiting 5-HT transport. Accordingly, the present compounds should be useful in treating disorders related to defects in serotonin concentration.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Any of the solid carriers known to those skilled in the art may be used with the compounds of this invention. Particularly suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidone, low melting waxes and ion exchange resins.

Liquid carriers may be used in preparing solutions, suspensions, emulsions, syrups and elixirs of the compounds of this invention. The compounds of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g., cellulose derivatives, preferably sodium carboxymethyl cellulose solution), alcohols (including monohydric alcohols and polyhydric alcohols, e.g., glycols) and their derivatives and oils (e.g., fractionated coconut oil and arachis oil). For parenteral administration, the carrier can also be an oily ester such as ethyl oleate and isopropyl myristate. Sterile liquid carriers are used in sterile liquid form compositions for parenteral administration.

Liquid pharmaceutical compositions which are sterile solutions or suspensions can be utilized by, for example, intramuscular, intraperitoneal or subcutaneous injection. Sterile solutions can also be administered intravenously. Compositions for oral administration may be either liquid or solid composition form.

Preferably, the pharmaceutical compositions containing the compounds of this invention are in unit dosage form, e.g., tablets or capsules. In such form, the compositions may be sub-divided in unit doses containing appropriate quantities of the present compounds. The unit dosage forms can be packaged compositions, for example, packeted powders, vials, ampoules, prefilled syringes or sachets containing liquids. Alternatively, the unit dosage form can be, for example, a capsule or tablet itself, or it can be the appropriate number of any such compositions in package form.

The therapeutically effective amount of the compounds of this invention that is administered and the dosage regimen depends on a variety of factors, including the weight, age, sex, and medical condition of the subject, the severity of the disease, the route and frequency of administration, and the specific compound employed, and thus may vary widely. However, it is believed that the pharmaceutical compositions may contain the compounds of this invention in the range of about 0.1 to about 2000 mg, preferably in the range of about 0.5 to about 500 mg and more preferably between about 1 and about 100 mg. Projected daily dosages of active compound are about 0.01 to about 100 mg/kg body weight. The daily dose can be conveniently administered two to four times per day.

The present invention may be embodied in other specific forms without departing from the spirit and essential attributes thereof and accordingly, reference should be made to the appended claims, rather than to the foregoing specification, as indicating the scope of the invention.

What is claimed is:
1. A compound of the formula:

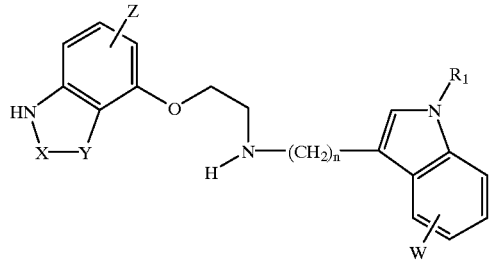

wherein:
$R_1$ is hydrogen, lower alkyl, phenyl, or substituted phenyl;
X and Y together complete a lactam, iridazole, imidazolone, or thioimidazolone ring;
Z is hydrogen, halogen, or lower alkoxy;
W is hydrogen, halogen, lower alkoxy, lower alkyl, cyano, or a trifluoromethyl group;
and n=2 to 5; or pharmaceutically acceptable salts thereof.

2. A compound as in claim 1, wherein:
$R_1$ is hydrogen;
X and Y together complete an imidazole or thioimidazolone ring;
Z is halogen or hydrogen;
W is halogen or hydrogen; and
n=2 to 3; or pharmaceutically acceptable salts thereof.

3. The compound of claim 1, which is [2-(3H-Benzoinidazol-4-yloxy)-ethyl]-[3-(1H-indol-3-yl)-propylamine.

4. The compound of claim 1, which is 4-{2-[3-1H-Indol-3-yl)-propylamino]-ethoxy}-1,3-dihydrobenzoimidazole-2-one.

5. The compound of claim 1, which is 4-{2-[3-1H-Indol-3-yl)-propylarnino]-ethoxy}-1,3-dihydrobenzoimidazole-2-thione.

6. The compound of claim 1, which is [2-(3H-Benzoimidazol-4-yloxy)-ethyl]-[3-(5-fluoro-1H-indol-3-yl)]-propyl]-amine.

7. The compound of claim 1, which is [2-(6-Chloro-1H-benzoirnidazol-4-yloxy)-ethyl]-[3-(5-fluoro-1H-indol-3-yl)]-propyl]-amine.

8. The compound of claim 1, which is 7-Fluoro-4-{2-[3-1H-indol-3-yl)-propylamino]-ethoxy }-1,3-dihydro-indol-2-one.

9. A pharmaceutical composition comprising a compound of the formula:

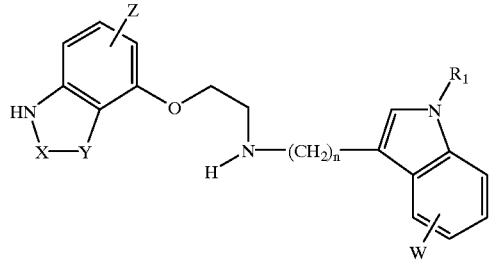

wherein:
$R_1$ is hydrogen, lower alkyl, phenyl, or substituted phenyl;

X and Y togethier complete a lactam, imidazole, imidazolone, or thioimdidazolone ring;

Z is hydrogen, halogen, or lower alkoxy;

W is hydrogen, halogen, lower alkoxy, lower alkyl, cyano, or a trifluoromethyl group;

and n=2 to 5; or pharmaceutically acceptable salts thereof.

10. A method for alleviating the symptoms of depression in a patient in need thereof comprising administering to said patient an antidepressant effective amount of a compound of the formula:

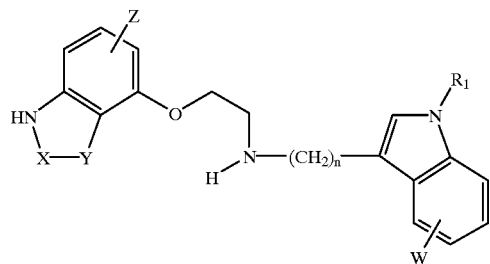

wherein:

$R_1$ is hydrogen, lower alkyl, phenyl, or substituted phenyl;

X and Y together complete a lactam, imidazole, imidazolone, or thioimidazolone ring;

Z is hydrogen, halogen, or lower alkoxy;

W is hydrogen, halogen, lower alkoxy, lower alkyl, cyano, or a trifluoromethyl group;

and n=2 to 5; or pharmaceutically acceptable salts thereof.

* * * * *